US00PP34824P2

(12) United States Plant Patent
Hofmann

(10) Patent No.: US PP34,824 P2
(45) Date of Patent: Dec. 13, 2022

(54) ***MANDEVILLA* PLANT NAMED 'INMANLIABR'**

(50) Latin Name: *Mandevilla sanderi*
Varietal Denomination: Inmanliabr

(71) Applicant: INNOVAPLANT ZIERPFLANZEN GmbH & Co. KG, Gensingen (DE)

(72) Inventor: Birgit Hofmann, Rudesheim am Rhein (DE)

(73) Assignee: INNOVAPLANT ZIERPFLANZEN GmbH + Co. KG, Gensingen (DE)

( * ) Notice: Subject to any disclaimer, the term of this patent is extended or adjusted under 35 U.S.C. 154(b) by 0 days.

(21) Appl. No.: 17/714,913

(22) Filed: Apr. 6, 2022

(51) Int. Cl.
*A01H 6/08* (2018.01)
*A01H 5/02* (2018.01)

(52) U.S. Cl.
USPC ..... Plt./232

(58) Field of Classification Search
USPC ..... Plt./232
See application file for complete search history.

*Primary Examiner* — Annette H Para
(74) *Attorney, Agent, or Firm* — C. Anne Whealy

(57) ABSTRACT

A new and distinct cultivar of *Mandevilla* plant named 'Inmanliapr', characterized by its compact, upright to broadly spreading plant habit; moderately vigorous to vigorous growth habit; freely branching habit; relatively small, glossy and medium green-colored leaves; early and freely flowering habit; and apricot-colored flowers with bright orange yellow-colored centers.

2 Drawing Sheets

Figure 1:
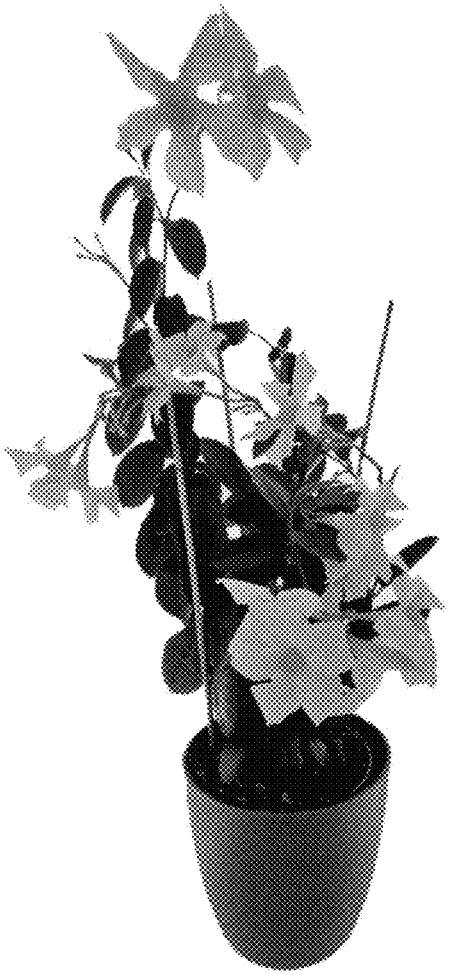

Botanical designation: *Mandevilla sanderi*.
Cultivar denomination: 'INMANLIABR'.

STATEMENT REGARDING PRIOR DISCLOSURES BY INVENTOR/APPLICANT AND ASSIGNEE

An European Community Plant Breeder's Rights application for the instant plant was filed by the Applicant/Assignee of the instant application, Innovaplant Zierpflanzen GmbH & Co. KG of Gensingen, Germany on Nov. 23, 2021, application number 2021/3018. Foreign priority is not claimed to this European Community Plant Breeder's Rights application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Mandevilla* plant, botanically known as *Mandevilla sanderi* and hereinafter referred to by the name 'Inmanliapr'.

The new *Mandevilla* plant is a product of a planned breeding program conducted by the Inventor in Heidesheim, Germany. The objective of the breeding program is to create new freely branching *Mandevilla* plants that flower early and freely and have attractive flowers that resist fading and sun scald.

The new *Mandevilla* plant originated from a cross-pollination conducted by the Inventor in Heidesheim, Germany in July, 2017 of *Mandevilla sanderi* 'Inmanwhimp', disclosed in U.S. Plant Pat. No. 28,276, as the female, or seed parent with *Mandevilla sanderi* 'Sunpapri', disclosed in U.S. Plant Pat. No. 28,277, as the male, or pollen, parent. The new *Mandevilla* plant was discovered and selected by the Inventor as a single flowering plant from within the progeny of the stated cross-pollination in a controlled greenhouse environment in Heidesheim, Germany in August, 2018.

Asexual reproduction of the new *Mandevilla* plant by vegetative cuttings in a controlled greenhouse environment in Heidesheim, Germany since August, 2018 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Inmanliapr'. These characteristics in combination distinguish 'Inmanliapr' as a new and distinct *Mandevilla* plant:

1. Compact, upright to broadly spreading plant habit.
2. Moderately vigorous to vigorous growth habit.
3. Freely branching habit.
4. Relatively small, glossy and medium green-colored leaves.
5. Early and freely flowering habit.
6. Apricot-colored flowers with bright orange yellow-colored centers.

Plants of the new *Mandevilla* can be compared to plants of the female parent, 'Inmanwhimp'. Plants of the new *Mandevilla* differ primarily from plants of 'Inmanwhimp' in the following characteristics:

1. Plants of the new *Mandevilla* have shorter leaves than plants of 'Inmanwhimp'.
2. Plants of the new *Mandevilla* have smaller flowers than plants of 'Inmanwhimp'.
3. Plants of the new *Mandevilla* have apricot-colored flowers whereas plants of 'Inmanwhimp' have white-colored flowers.

Plants of the new *Mandevilla* can be compared to plants of the male parent, 'Sunpapri'. Plants of the new *Mandevilla* differ primarily from plants of 'Sunpapri' in the following characteristics:

1. Plants of the new *Mandevilla* have smaller leaves than plants of 'Sunpapri'.
2. Plants of the new *Mandevilla* have smaller flowers than plants of 'Sunpapri'.
3. Plants of the new *Mandevilla* flower earlier than plants of 'Sunpapri'.

Plants of the new *Mandevilla* can also be compared to plants of *Mandevilla hybrida* 'Sunpa 2675', not patented. In side-by-side comparisons, plants of the new *Mandevilla* differ primarily from plants 'Sunpa 2675' in the following characteristics:

1. Leaves of plants of the new *Mandevilla* are not as glossy as leaves of plants of 'Sunpa 2675'.
2. Plants of the new *Mandevilla* have apricot-colored flowers with bright orange yellow-colored centers whereas plants of 'Sunpa 2675' have light yellow-colored flowers with dark yellow-colored centers with orange-colored stripes.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet (FIG. 1) is a side perspective view of a typical flowering plant of 'Inmanliapr' grown in a container.

Figure 2:
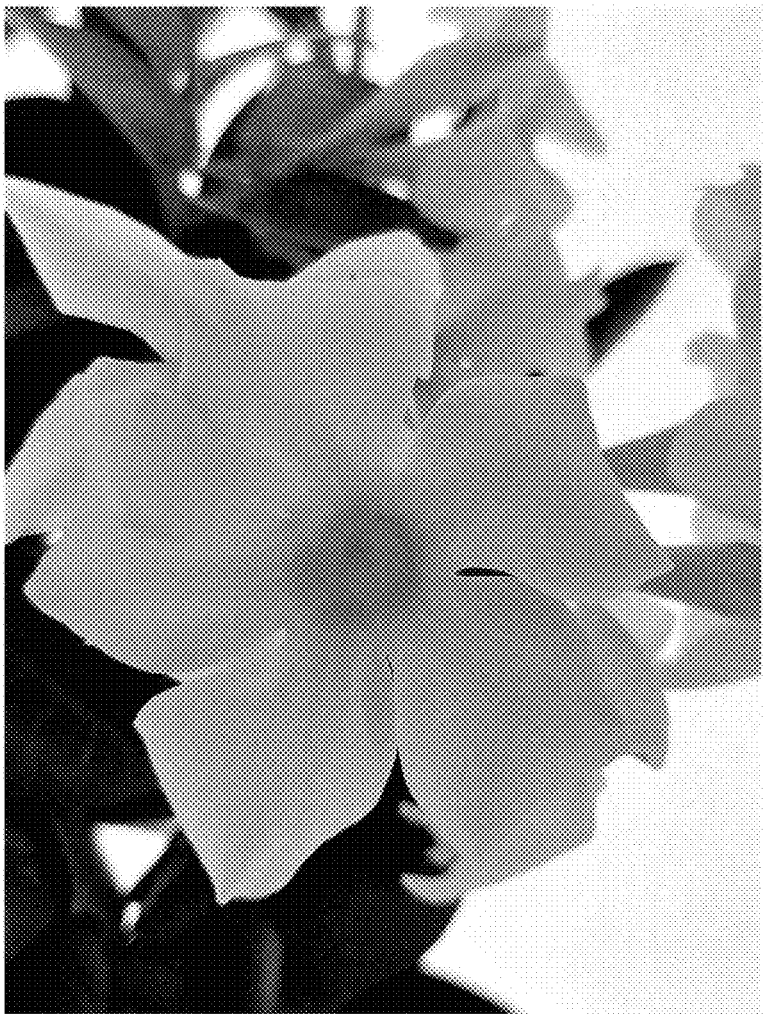

The photograph on the second sheet (FIG. 2) is a close-up view of a typical flowering plant of 'Inmanliapr'.

DETAILED BOTANICAL DESCRIPTION

The aforementioned photographs and following observations, measurements and values describe plants grown during the summer in 12-cm containers in a glass-covered greenhouse in Heidesheim, Germany and under cultural practices typical of commercial *Mandevilla* production. During the production of the plants, day temperatures ranged from 12° C. to 35° C. and night temperatures ranged from 12° C. to 18° C. Plants were pinched one time four weeks after planting and were three months old when the photographs and description were taken. In the following description, color references are made to The Royal Horticultural Society Colour Chart, 2015 Edition, except where general terms of ordinary dictionary significance are used.

Botanical classification: *Mandevilla sanderi* 'Inmanliapr'.

Parentage:

*Female, or seed, parent.*—*Mandevilla sanderi* 'Inmanwhimp', disclosed in U.S. Plant Pat. No. 28,276.

*Male, or pollen, parent.*—*Mandevilla sanderi* 'Sunpapri', disclosed in U.S. Plant Pat. No. 28,277.

Propagation:

*Type.*—By vegetative cuttings.

*Time to initiate roots, summer and winter.*—About three weeks at temperatures ranging from 20° C. to 35° C.

*Time to produce a rooted young plant, summer.*—About 20 to 25 days at temperatures ranging from 20° C. to 35° C.

*Time to produce a rooted young plant, winter.*—About 25 to 30 days at temperatures ranging from 20° C. to 25° C.

*Root description.*—Thick, fleshy; typically white in color, actual color of the roots is dependent on substrate composition, water quality, fertilizers, substrate temperature and physiological age of roots.

*Rooting habit.*—Low branching; medium density.

Plant description:

*Plant and growth habit.*—Compact, upright to broadly spreading plant habit; roughly obovate in overall shape; moderately vigorous to vigorous growth habit and moderate growth rate.

*Plant height, soil level to top of foliar plane.*—About 30 cm.

*Plant height, soil level to top of floral plane.*—About 39.9 cm.

*Plant diameter (spread).*—About 34.9 cm.

*Lateral branch description.*—Branching habit: Freely branching habit, typically about three primary lateral branches each with about three secondary lateral branches. Length: About 10.2 cm. Diameter: About 3 mm. Internode length: About 4.2 cm. Aspect: Primary lateral branches, mostly upright; secondary lateral branches, about 15° to 30° from primary branch axis. Strength: Strong. Texture and luster: Smooth, glabrous; slightly glossy; becoming woody with development. Color, developing and developed: Close to a blend of 144A and 144B; when woody, close to N199A to N199D.

Leaf description:

*Arrangement.*—Opposite, simple.

*Length.*—About 6.3 cm.

*Width.*—About 3.8 cm.

*Shape.*—Oblong to somewhat obovate; slightly carinate.

*Apex.*—Abruptly acute.

*Base.*—Truncate to obtuse.

*Margin.*—Entire.

*Texture and luster, upper and lower surfaces.*—Smooth, glabrous; moderately coriaceous; glossy.

*Venation pattern.*—Pinnate.

*Color.*—Developing leaves, upper surface: Close to 143A to 143B. Developing leaves, lower surface: Close to 145B. Full expanded leaves, upper surface: Slightly darker than NN137A; venation, close to 143B to 143C. Fully expanded leaves, lower surface: Close to a blend of 146B and 146C; venation, close to 145C.

*Petioles.*—Length: About 1 cm. Diameter: About 2 mm by 2.5 mm. Strength: Moderately strong. Texture and luster, upper and lower surfaces: Smooth, glabrous; moderately glossy. Color, upper and lower surfaces: Close to 145A.

Flower description:

*Flower type and flowering habit*.—Single salverform flowers arranged in terminal and axillary cymes; flowers face outwardly to slightly upright; freely flowering habit with about seven flowers per inflorescence and about 65 flower buds and open flowers developing per plant during the flowering season.

*Natural flowering season*.—Plants flower continuously from spring into the autumn in Germany; plants begin flowering about 13 weeks after propagation (dependent on light level).

*Flower longevity on the plant*.—Individual flowers last about two weeks; flowers not persistent.

*Fragrance*.—None detected.

*Inflorescence height*.—About 13.4 cm.

*Inflorescence diameter*.—About 10.9 cm.

*Flower buds*.—Length: About 5.7 cm. Diameter: About 1 cm. Shape: Narrowly oblanceolate. Texture and luster: Smooth, glabrous; slightly glossy. Color: Distally, close to 162C with apex, close to 18A; proximally, lighter than 153D and tube, close to 150A.

*Flowers*.—Appearance: Flared trumpet, corolla fused and five-parted. Diameter: About 7.5 cm by 7.5 cm. Depth (length): About 6 cm. Throat diameter: About 1.7 cm. Tube length: About 4.1 cm. Tube diameter: Proximally, about 3 mm; distally, about 1.4 cm.

*Corolla*.—Quantity and arrangement: Five petals arranged in a single whorl; lower 53% portion of the petals are fused into a funnelform tube. Petal length: About 7.7 cm. Petal width: About 3.2 cm. Petal shape and appearance: Roughly unequal spatulate; strongly convex. Petal apex: Apiculate, unequal. Petal margin: Entire; coarsely revolute and moderately undulate. Petal texture and luster, upper and lower surfaces: Smooth, glabrous; slightly velvety; slightly glossy. Throat texture: Smooth, glabrous; velvety. Tube texture: Smooth, glabrous; slightly velvety. Color: Petal, when opening, upper surface: Close to a blend of 26C and 26D with apex, close to 31D and flushed with close to 24A towards the throat. Petal, when opening, lower surface: Close to 26D; midvein and adjacent area, close to 18B. Petal, fully opened, upper surface: Close to 27A to slightly darker than 27A; towards the apex and margins, close to a blend of 24C to 24D and 29C; flushed with close to 21B towards the throat; venation, similar to lamina; color becoming closer to 27D and flushed with close to 22B to 22C towards the throat with subsequent development. Petal, fully opened, lower surface: Close to 27A and towards the tube, close to 19B to 19C; venation, close to 18C; color becoming closer to 27D with subsequent development. Throat: Close to 23B; proximally, close to 25A and at the base of the throat, close to 151B; venation, similar to lamina colors or close to 17A. Tube: Mid-section, close to 14B; distally, close to 19B and proximally, close to 153D and 151B; venation, similar to lamina colors.

*Sepals*.—Quantity and arrangement: Five sepals arranged in a single whorl. Length: About 8 mm. Width: About 2 mm. Shape: Lanceolate. Apex: Narrowly acuminate. Base: Broadly cuneate and fused. Margin: Entire. Texture and luster, upper surface: Smooth, glabrous; slightly glossy. Texture and luster, lower surface: Smooth, glabrous; matte. Color: When developing, upper surface: Close to 145C; towards the base, close to 145A; apex, close to 179B. When developing, lower surface: Close to 145B; towards the base, close to 145A; apex, close to 179A to 179B. Fully opened, upper surface: Close to 145B; towards the base, close to 145A; apex, close to 179B; at the margins, close to 145C. Fully opened, lower surface: Close to 145B; towards the base, close to 145A; apex, close to 179A.

*Peduncles*.—Length: About 8.5 cm. Diameter: About 2 mm. Strength: Strong. Aspect: About 15° to 45° from lateral branch axis. Texture and luster: Smooth, glabrous; moderately glossy. Color: Close to a blend of 144A and 146A.

*Pedicels*.—Length: About 1.7 cm. Diameter: About 2 mm. Strength: Strong. Aspect: About 20° to 60° from peduncle axis. Texture and luster: Smooth, glabrous; slightly glossy. Color: Close to 144B.

*Reproductive organs*.—Stamens: Quantity and arrangement: Typically five; basifixed; anthers connivent. Filament length: About 5 mm. Filament color: Close to 153D. Anther shape: Narrowly oblong. Anther size: About 1.25 mm by 7 mm. Anther color: Close to 163C. Pollen amount: None observed. Pistils: Quantity: Typically one. Pistil length: About 2 cm. Style length: About 1.75 cm. Style color: Close to 145D. Stigma diameter: About 2 mm. Stigma shape: Club-shaped, pointed. Stigma color: Close to 153C. Ovary color: Close to 145A.

*Seeds and fruits*.'To date, seed and fruit production have not been observed on plants of the new *Mandevilla*.

Pathogen & pest resistance: To date, plants of the new *Mandevilla* have not been noted to be resistant to pathogens and pests common to *Mandevilla* plants.

Temperature tolerance: Plants of the new *Mandevilla* have been observed to tolerate temperatures ranging from about 5° C. to about 40° C. and to be suitable for USDA Hardiness Zones 9 to 13.

It is claimed:

1. A new and distinct *Mandevilla* plant named 'Inmanliapr' as illustrated and described.

* * * * *